United States Patent
Schroeder et al.

(10) Patent No.: US 6,716,438 B1
(45) Date of Patent: Apr. 6, 2004

(54) USE OF NANOSCALAR ANTIMICROBIAL ACTIVE INGREDIENTS IN BODY DEODORANTS

(75) Inventors: Christine Schroeder, Duesseldorf (DE); Hans-Theo Leinen, Duesseldorf (DE); Bernhard Banowski, Duesseldorf (DE); Marcel Roth, Duesseldorf (DE); Johann Glasl, Solingen (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/018,274

(22) PCT Filed: Apr. 22, 2000

(86) PCT No.: PCT/EP00/03659

§ 371 (c)(1), (2), (4) Date: Jun. 10, 2002

(87) PCT Pub. No.: WO00/66074

PCT Pub. Date: Nov. 9, 2000

(30) Foreign Application Priority Data

Apr. 30, 1999 (DE) .......................................... 199 19 769

(51) Int. Cl.$^7$ ............................ A61K 7/00; A61K 7/32; A01N 25/34
(52) U.S. Cl. ......................... 424/401; 424/65; 424/404
(58) Field of Search ............................ 424/401, 65, 404

(56) References Cited

U.S. PATENT DOCUMENTS 3,800,048 A * 3/1974 Model et al. ............... 424/405
5,169,631 A   12/1992 Rase et al.
5,453,268 A   9/1995 Ueno et al.
6,552,214 B1 * 4/2003 Modello et al. ............ 556/447

FOREIGN PATENT DOCUMENTS

| | | |
|---|---|---|
| CA | 2111522 | 6/1994 |
| CA | 2111523 | 6/1994 |
| DE | 1 165 574 | 3/1964 |
| DE | 2 024 051 | 12/1971 |
| DE | 44 02 103 | 7/1994 |
| EP | 0 200 548 | 11/1986 |
| EP | 0 423 002 | 4/1991 |
| GB | 962919 | 7/1964 |
| GB | 1 333 475 | 10/1973 |
| JP | 09 299460 | 11/1997 |
| WO | WO 90/10635 | 9/1990 |
| WO | WO 98/14174 | 4/1998 |

OTHER PUBLICATIONS

S. Chihlar, M. Türk and K. Schaber, Proceedings World Congress on Particle Technology 3, Brighton, (1998), pp. 1–11.

* cited by examiner

Primary Examiner—Shelley A. Dodson
(74) Attorney, Agent, or Firm—John E. Drach

(57) ABSTRACT

A deodorant composition and method of making and using a deodorant composition are provided. The deodorant composition contains nanoscale antimicrobial particles where the nanoscale antimicrobial particles contain one or more antimicrobial agents and have a particle diameter in the range of from 5 nanometers to 500 nanometers.

21 Claims, No Drawings

USE OF NANOSCALAR ANTIMICROBIAL ACTIVE INGREDIENTS IN BODY DEODORANTS

CROSS REFERENCE TO RELATED APPLICATIONS

This application is a national stage application under 35 U.S.C. §371 of international application PCT/EP00/03659 filed on Apr. 22, 2000, the international application not being published in English. This application also claims priority under 35 U.S.C. §119 to DE 199 19 769.5 filed on Apr. 30, 1999.

BACKGROUND OF THE INVENTION

This invention relates to the use of antimicrobial agents in nanoscale form for the production of body deodorants.

Body deodorants, also known simply as deodorants, are formulations which counteract, mask or eliminate body odors. Body odors are formed by the action of skin bacteria on apocrine perspiration which results in the formation of unpleasant-smelling degradation products. Accordingly, deodorants contain active principles which act as antibacterial agents, enzyme inhibitors, odor absorbers or odor maskers.

Nanoscale materials are materials whose particle diameter in the direction of the largest dimension of the particles is less than 1000 nm (nanometers). In the present specification, the term "nanoparticulate" is used synonymously with the term "nanoscale". Nanoscale active principles are described in the literature in particular as agents for achieving a controlled release of the active principle over a prolonged period. For example, WO 98/14174 describes nanoparticles for parenteral therapeutic use which consist of a pharmacologically active substance encapsulated in a shell of a biodegradable polymer. The document in question mentions inter alia antibacterial agents, such as chloramphenicol and vanomycin, and antimicrobial agents, such as penicillins and cephalosporins, as examples of pharmacologically active substances. Antimicrobial products containing nanoscale Schiff—s bases of aromatic aldehydes are known from DE 4402103 which describes the use of these products for the lasting antimicrobial finishing of textiles. Patent application CA 2,111,523 describes disinfectants which, besides other constituents, also contain surface-modified nanoparticulate antimicrobial agents. A disinfecting cleaner formulation is mentioned as an example. Patent application CA 2,111,522 describes compositions with a long-lasting germicidal effect which contain surface-modified nanoparticulate antimicrobial agents. Disinfectants for surface treatment which form permanent antimicrobial films on the treated surface are mentioned as applications of these compositions. However, there is nothing in the prior art to suggest that nanoparticulate antimicrobial agents can be used with advantage as active principles in body deodorants. Although it is known to the expert that antimicrobial agents are used, for example, both in surface disinfection and in body deodorants, the expert also knows that the form of application and the requirements in regard to strength of effect, action spectrum and the formulation of the active principles are so different in the various fields of application that the knowledge acquired in one field of application cannot obviously be applied to another field of application.

Because of their physiochemical properties and their own odors, the active principles used in body deodorants are often attended in practice by the problem that they only be incorporated in deodorant formulations with difficulty or in inadequate concentrations so that the formulations obtained show unsatisfactory antimicrobial activity. In addition, there is a demand among consumers for body deodorants which work with reduced concentrations of the active principle without any loss of deodorizing effect and hence offer physiological, economic and/or ecological advantages.

Accordingly, one problem addressed by the present invention was to enable body deodorants to be produced using antimicrobial agents which, due for example to their poor solubility or their strong odor, can only be conventionally incorporated in body deodorants with difficulty or in inadequate concentrations.

Another problem addressed by the invention was to provide body deodorants with sufficient antimicrobial activity for practical application and, at the same time, a reduced content of antimicrobial agents.

The problems stated above have been solved by the use of the antimicrobial agents in the form of nanoparticles with a particle diameter of 5 to 500 nm and preferably 10 to 150 nm for the production of body deodorants.

SUMMARY OF THE INVENTION

In a first embodiment, therefore, the present invention relates to the use of nanoscale antimicrobial agents with a particle diameter of 5 to 500 nm and preferably 10 to 150 nm for the production of body deodorants, more especially deodorizing aerosols, pump sprays, roll-ons and sticks. The use of the nanoscale antimicrobial agents is particularly suitable for the production of products which are required to show only bacteriostatic activity and not bactericidal activity.

It has surprisingly been found that the following advantages, for example, are achieved in this way:

a) The incorporation of antimicrobial agents in deodorant formulations is improved to the extent that lipophilic active principles can be incorporated more easily in aqueous formulations while hydrophilic active principles can be incorporated more easily in nonaqueous or low-water formulations.

b) the effectiveness of the active principles from the formulations is increased. This means that, for the same quantity by weight, the nanoparticulate active principle has a stronger antimicrobial effect than the same active principle in a larger particle size corresponding to the prior art.

c) In the case of active principles with a strong odor of their own, the odor can be weakened or even suppressed by surface modification of the nanoscale particles.

DETAILED DESCRIPTION OF THE INVENTION

Antibacterial agents with substantially selective activity against bacteria involved in the formation of odor-generating substances in bodily perspiration are particularly suitable for the use according to the invention. Where antimicrobial agents are used, it is important to ensure that the population of the bacteria concerned is merely controlled to prevent excessive growth (bacteriostatic effect) and not to destroy the bacteria completely (which would correspond to bactericidal activity).

Any substances active against gram-positive bacteria are particularly suitable as antimicrobial agents according to the invention. Substances active against Corynebacterium xero sis are particularly preferred. The active substances according to the invention include, for example,

- 4-hydroxybenzoic acid, its salts with alkali or alkaline earth metals or its esters with linear or branched $C_{1-10}$ alcohols,
- N-(4-chlorophenyl)-N'-(3,4-dichlorophenyl)-urea,
- 2,4,4'-trichloro-2'-hydroxy diphenyl ether (triclosan),
- 4-chloro-3,5-dimethyl phenol,
- 2,2'-methylene-bis-(6-bromo-4-chlorophenol),
- 3-methyl-4-(1-methylethyl)-phenol,
- 2-benzyl-4-chlorophenol,
- 3-(4-chloropenoxy)-propane-1,2-diol,
- 3-iodo-2-propinyl butyl carbamate,
- chlorohexidine,
- 3,4,4'-trichlorocarbanilide (TTC),
- 1-hydroxy-4-methyl-6-(2,4,4-trimethylpentyl )-2-(1H)-pyridinone, ethanolamine salt (1:1) (Octopirox)
- antimicrobial perfumes such as, for example, thymol or menthol,
- glycerol monolaurate (GML),
- diglycerol monocaprate (DMC),
- zinc salts such as, for example, zinc glycinate, zinc lactate or zinc phenol sulfonate,
- phytosphingosines,
- dodecane-1,2-diol,
- undecylenic acid, its salts with alkali or alkaline earth metals or its esters with linear or branched $C_{1-10}$ alcohols,
- salicylic acid-N-alkyl amides where the alkyl groups contain 1 to 22 carbon atoms and may be linear or branched and mixtures thereof.

Particularly preferred antimicrobial agents according to the invention are salicylic acid-N-octyl amide and/or salicylic acid-N-decyl amide, 2,4,4'-trichloro-2'-hydroxydiphenyl ether and antimicrobially active perfumes.

The nanoscale active principles consist of a discrete phase of the active principle with preferably at least one surface modifier adsorbed onto its surface. Particularly suitable surface modifiers are emulsifiers and/or protective colloids. The coating of the particles with emulsifiers and/or protective colloids prevents subsequent agglomeration of the particles.

Suitable emulsifiers are, for example, nonionic surfactants from at least one of the following groups:

(1) products of the addition of 2 to 30 moles of ethylene oxide and/or 0 to 5 moles of propylene oxide onto linear $C_{8-22}$ fatty alcohols, $C_{12-22}$ fatty acids and alkyl phenols containing 8 to 15 carbon atoms in the alkyl group;

(2) $C_{12/18}$ fatty acid monoesters and diesters of addition products of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) products of the addition of 15 to 60 moles of ethylene oxide onto castor oil and/or hydrogenated castor oil;

(6) polyol esters and, in particular, polyglycerol esters such as, for example, polyglycerol polyricinoleate, polyglycerol poly-12-hydroxy stearate or polyglycerol dimerate. Mixtures of compounds from several of these classes are also suitable;

(7) products of the addition of 2 to 15 moles of ethylene oxide onto castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), sucrose, alkyl glucosides (for example methyl glucoside, butyl glucoside, lauryl glucoside) and polyglucosides (for example cellulose);

(9) mono-, di and trialkyl phosphates and mono-, di- and/or tri-PEG-alkyl phosphates and salts thereof;

(10) wool wax alcohols;

(11) polysiloxanelpolyalkyl polyether copolymers and corresponding derivatives;

(12) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol or polyglycerol, and

(13) polyalkylene glycols.

The addition products of ethylene oxide and/or propylene oxide onto fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as refatting agents for cosmetic formulations from DE-PS 20 24 051.

$C_{8/18}$ alkyl mono- and oligoglycosides, their production and their use are known from the prior-art literature. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

Typical examples of anionic emulsifiers are soaps, alkyl benzene-sulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuc cinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl-(ether) phosphates. If the anionic surfactants contain polyglycol ether chains, they may have a conventional homolog distribution although they preferably have a narrow-range homolog distribution.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of *Cocamidopropyl Betaine* is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. According to the invention, other suitable emulsifiers besides ampholytic surfactants are quaternary emulsifiers, those of the esterquat type, preferably methylquaternized difatty acid triethanolamine ester salts, being particularly preferred. Typical examples of anionic emulsifiers are alkyl sulfates, alkyl ether sulfates and monoglyceride (ether) sulfates.

In general, the active principles and the emulsifiers are used in a ratio by weight of 1:100 to 100:1, preferably 1:25 to 25:1 and more preferably 1:10 to 10:1. Emulsifiers capable of forming microemulsions are particularly preferred.

Suitable protective colloids are, for example, gelatine, casein, gum arabic, lysalbinic acid, starch, carboxymethyl cellulose or modified carboxymethyl cellulose and polymers such as, for example, polyvinyl alcohols, polyvinyl pyrrolidones, polyalkylene glycols and polyacrylates.

Accordingly, the present invention also relates to the use according to the invention of nanoscale antimicrobial agents where the nanoparticles are coated with one or more emulsifiers and/or protective colloids.

The nanoparticles according to the invention can be produced, for example, by
  (a) introducing active principles into a liquid phase in which they are insoluble,
  (b) heating the resulting mixture to beyond the melting point of the active principles,
  (c) adding an effective quantity of at least one emulsifier to the resulting oil phase and finally
  (d) cooling the emulsion to below the melting point of the active principles.

Accordingly, the present invention also relates to the use according to the invention of nanoscale antimicrobial agents produced by this process.

Another process for the production of nanoparticles by rapid expansion of supercritical solutions (RESS) is known from the article by S. Chihlar, M. Türk and K. Schaber in *Proceedings World Congress on Particle Technology* 3, *Brighton*, 1998. To prevent the nanoparticles from re-agglomerating, it is advisable to dissolve the starting materials in the presence of suitable protective colloids or emulsifiers and/or to expand the critical solutions into aqueous and/or alcoholic solutions of the protective colloids or emulsifiers or into cosmetic oils which may in turn contain redissolved emulsifiers and/or protective colloids.

Another suitable process for the production of nanoscale particles is the evaporation technique. Here, the starting materials are first dissolved in a suitable organic solvent (for example alkanes, vegetable oils, ethers, esters, ketones, acetals and the like). The resulting solutions are then introduced into water or another non-solvent, generally in the presence of a surface-active compound dissolved therein, in such a way that the nanoparticles are precipitated by the homogenization of the two immiscible solvents, the organic solvent preferably evaporating. O/w emulsions or o/w microemulsions may be used instead of an aqueous solution. The emulsifiers and protective colloids mentioned at the beginning may be used as the surface-active compounds. Another method for the production of nanoparticles is the so-called GAS process (gas anti-solvent recrystallization). This process uses a highly compressed gas or supercritical fluid (for example carbon dioxide) as non-solvent for the crystallization of dissolved substances. The compressed gas phase is introduced into the primary solution of the starting materials and absorbed therein so that there is an increase in the liquid volume and a reduction in solubility and fine particles are precipitated. The PCA process (precipitation with a compressed fluid anti-solvent) is equally suitable. In this process, the primary solution of the starting materials is introduced into a supercritical fluid which results in the formation of very fine droplets in which diffusion processes take place so that very fine particles are precipitated. In the PGSS process (particles from gas saturated solutions), the starting materials are melted by the introduction of gas under pressure (for example carbon dioxide or propane). Temperature and pressure reach near- or super-critical conditions. The gas phase dissolves in the solid and lowers the melting temperature, the viscosity and the surface tension. On expansion through a nozzle, very fine particles are formed as a result of cooling effects.

The above-mentioned production processes for the nanoparticles according to the invention are merely examples and are not intended to limit the invention in any way.

The body deodorants obtainable using the nanoscale antimicrobial agents in accordance with the invention may also contain, for example, fatty acids in the form of their alkali metal soaps, polyols, lower alcohols, enzyme inhibitors, odor absorbers, odor maskers, water, complexing agents, antioxidants, preservatives, perfumes, colorants, opacifiers, pearlizing pigments, fine-particle silica, consistency factors, gel formers, waxes, fatty alcohols, emulsifiers, thickeners and other suitable formulation bases as further auxiliaries and additives.

Fatty acids in the context of the invention are $C_{16-22}$ carboxylic acids such as, for example, palmitic acid, stearic acid and behenic acid or technical mixtures consisting predominantly of such fatty acids, for example hydrogenated palm oil fatty acid or hydrogenated tallow fatty acid.

Polyols in the context of the invention are those containing 3 to 6 carbon atoms and 2 to 6 hydroxyl groups such as, for example, ethylene glycol, 1,2-propylene glycol, 1,3-propylene glycol, 1,2-butylene glycol, 1,3-butylene glycol, 1,4-butylene glycol, glycerol, erythritol, pentaerythritol, trimethylol propane, sorbitol, anhydrosorbitol, cyclohexane triol or inositol.

The preparations may contain ethanol or isopropanol, for example, as lower alcohols.

Suitable enzyme inhibitors are, for example, esterase inhibitors. Esterase inhibitors are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Suitable odor absorbers are substances which are capable of absorbing and largely retaining the odor-forming compounds. They reduce the partial pressure of the individual components and thus also reduce the rate at which they spread. An important requirement in this regard is that perfumes must remain unimpaired. Odor absorbers are not active against bacteria. They contain, for example, a complex zinc salt of ricinoleic acid or special perfumes of largely neutral odor known to the expert as "fixateurs" such as, for example, extracts of ladanum or styrax or certain abietic acid derivatives as their principal component. Odor maskers are perfumes or perfume oils which, besides their odor-masking function, impart their particular perfume note to the deodorants. Suitable perfume oils are, for example, mixtures of natural and synthetic fragrances. Natural fragrances include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert butyl cyclohexylacetate, linalyl acetate, phenyl ethyl acetate, linalyl, benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

In order to be able to apply the active principles to the skin in a measurable, economic, convenient and cosmetically attractive manner, they have to be incorporated in suitable formulation bases. The most important of these are alcoholic and aqueous/alcoholic solutions, emulsions, gels, sticks—for example glycolic soap sticks—oils, wax/fat compounds and powders. Stabilizers, consistency factors and foam inhibitors, for example, may be used as additional auxiliaries.

Suitable supply forms for deodorants are aerosols, pump sprays, roll-ons, sticks and gels and also creams and powders.

The quantity in which the nanoscale compounds are used is selected so that the concentration of the antimicrobial agents present in the nanoparticles is normally between 0.01 and 5% by weight and preferably between 0.1 and 2% by weight, based on the preparations.

To produce the body deodorants according to the invention, the nanoscale antimicrobial agents are mixed with the other formulation ingredients in known manner.

The present invention also relates to body deodorants containing antimicrobial agents which are characterized in that the antimicrobial agent is incorporated in the form of nanoparticles with a particle diameter of 5 to 500 nm and preferably 10 to 150 nm.

Other embodiments and/or further developments are covered by the subsidiary claims.

EXAMPLES

The following Examples are intended to illustrate the invention.

Example 1

Prepararation of Sanoscale Nalicylic Acid-N-octyl Amide 0.5 g of salicylic acid-N-octyl amide (Mp. ca. 45° C.) were dissolved in 100 g of deionized water and the mixture was heated to around 50° C., resulting in the formation of a two-phase mixture of water and amide phase. The amide phase was emulsified by addition of 8.9 g of alkyl ether sulfate (Texapon® N 70, Henkel KGaA, Düsseldorf) to form a clear mixture. The gradual passing of the oil phase into the transparent water/amide/emulsifier mixture may be taken as an indication of the formation of a microemulsion. The microemulsion was cooled to ambient temperature with continued stirring and was then concentrated by evaporation to dryness in a rotary evaporator, 9.4 g of the salicylic acid-N-octyl amide encapsulated in the ether sulfate matrix being obtained in nanoparticulate form. The nanoparticles could be reprocessed with ten times the quantity of water to form a stable and transparent dispersion. In light scattering, the particles showed a maximum with numerical weighting at a particle size of 120 nm.

Example 2

Preparation of a Nanoscale Aqueous Salicylic Acid-N-octyl Amide Dispersion 1.0 g of salicylic acid-N-octyl amide (Mp. ca. 45° C.) were emulsified with 30 g of deionized water, 30 g of Polydiol 400 (PEG-8) and 2 g of polyoxyethylene glycerol fatty acid ester (Tagat S) and slowly heated to 52° C. 30 g of fatty acid amidoalkyl betaine (Tego Betain BL 215) were then added, a clear stable dispersion being formed. The mixture was then allowed to cool to room temperature. 93 g of a transparent dispersion were obtained. In light scattering, the particles showed a maximum with numeral weighting at a particle size of 15 nm.

Example 3

Formulation Example for a deodorizing pump spray formulation:

| Ingredient | Content (% by weight) |
|---|---|
| Hydrogenated castor oil + 40 moles EO (Eumulgin HRE, Henkel KGaA) | 2 |
| Aqueous dispersion of nanoscale salicylic acid-N-octyl amide from Example 2 | 10 |
| Perfume oil | 0.3 |
| Glycerol | 7.7 |
| Water | 80 |

What is claimed is:

1. A method of making a body deodorant comprising forming a deodorant composition comprising nanoscale antimicrobial particles wherein the nanoscale antimicrobial particles comprise one or more antimicrobial agents and have a particle diameter in the range of from about 5 nanometers to about 500 nanometers.

2. The method of claim 1 wherein the antimicrobial agents are active against gram-positive bacteria.

3. The method of claim 2 wherein the antimicrobial agents are active against Corynebacterium xerosis.

4. The method of claim 3 wherein the antimicrobial agents comprise salicylic acid-n-octyl amide, or salicylic acid-n-decyl amide, or combinations thereof.

5. The method of claim 3 wherein the antimicrobial agents comprise 2,4,4'-trichloro-2'-hydroxydiphenyl ether.

6. The method of claim 1 wherein the nanoscale antimicrobial particles are obtained by a process comprising:
   (a) adding the antimicrobial agents into a liquid phase to form a liquid mixture, wherein the antimicrobial agents are insoluble in the liquid phase;
   (b) heating the liquid mixture to at least a temperature beyond the melting point of the antimicrobial agents;
   (c) adding an effective quantity of at least one emulsifier to the liquid mixture to form an emulsion; and
   (d) cooling the emulsion to below the melting point of the antimicrobial agents.

7. The method of claim 1 wherein the antimicrobial agents comprise an antimicrobial perfume.

8. The method of claim 1 wherein the antimicrobial agents comprise salicylic acid-n-octyl amide, or salicylic acid-n-decyl amide, or combinations thereof.

9. The method of claim 1 wherein the nanoscale antimicrobial particles are coated with a coating comprising one or more emulsifiers, or protective colloids, or mixtures thereof.

10. The method of claim 1 wherein the nanoscale antimicrobial particles comprise from about 0.01 wt % to about 5 wt % of the antimicrobial agents based on the total weight of the nanoscale particles.

11. The method of claim 1 wherein the deodorant composition is in the form of a deodorizing aerosol, pump spray, roll-on preparation, or stick preparation.

12. A body deodorant composition comprising nanoscale antimicrobial particles wherein the nanoscale antimicrobial particles comprise one or more antimicrobial agents and have a particle diameter in the range of from about 5 nanometers to about 500 nanometers.

13. The composition of claim 12 wherein the antimicrobial agents are active against Corynebacterium xerosis.

14. The composition of claim 13 wherein the nanoscale antimicrobial particles comprise from about 0.01 wt % to about 5 wt % of the antimicrobial agents based on the total weight of the nanoscale particles.

15. The composition of claim 14 wherein the deodorant composition is in the form of a deodorizing aerosol, pump spray, roll-on preparation, or stick preparation.

16. The composition of claim 15 wherein the antimicrobial agents comprise salicylic acid-n-octyl amide, or salicylic acid-n-decyl amide, or combinations thereof.

17. The composition of claim 15 wherein the antimicrobial agents comprise 2,4,4'-trichloro-2'-hydroxydiphenyl ether.

18. A method of preventing or treating body odors comprising:
   (a) providing a deodorant composition comprising nanoscale antimicrobial particles wherein the nanoscale antimicrobial particles comprise one or more antimicrobial agents and have a particle diameter in the range of from about 5 nanometers to about 500 nanometers; and
   (b) applying the deodorant composition to a body.

19. The method of claim 18 wherein the nanoscale antimicrobial particles comprise from about 0.01 wt % to about 5 wt % of the antimicrobial agents based on the total weight of the nanoscale particles.

20. The method of claim 19 wherein the deodorant composition is in the form of a deodorizing aerosol, pump spray, roll-on preparation, or stick preparation.

21. The method of claim 19 wherein the antimicrobial agents comprise salicylic acid-n-octyl amide, or salicylic acid-n-decyl amide, or combinations thereof.

* * * * *